(12) United States Patent
Phillion et al.

(10) Patent No.: US 8,669,407 B2
(45) Date of Patent: Mar. 11, 2014

(54) METHOD OF ISOLATING LINEAR BUTENES FROM A MIXED HYDROCARBON FEED

(75) Inventors: Katherine Sullivan Phillion, Nassau Bay, TX (US); Garland B. Brignac, Clinton, LA (US); Michael C. Clark, Chantilly, VA (US); Glenn J. Moloney, Houston, TX (US); Donald J. Norris, London (CA); Benjamin S. Umansky, Fairfax County, VA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 787 days.

(21) Appl. No.: 12/200,468

(22) Filed: Aug. 28, 2008

(65) Prior Publication Data

US 2010/0056834 A1    Mar. 4, 2010

(51) Int. Cl.
*C07C 2/12* (2006.01)
*C07C 7/177* (2006.01)

(52) U.S. Cl.
USPC ........... 585/533; 585/520; 585/530; 585/532; 585/809; 585/833; 585/851; 585/852

(58) Field of Classification Search
USPC .......... 422/188; 585/832, 820, 502, 520, 532, 585/533, 530, 809, 833, 851, 852
See application file for complete search history.

(56) References Cited

U.S. PATENT DOCUMENTS

| | | | | |
|---|---|---|---|---|
| 3,531,539 A | * | 9/1970 | Tidwell | 585/251 |
| 4,313,016 A | * | 1/1982 | Manning | 585/832 |
| 4,356,339 A | * | 10/1982 | Imaizumi et al. | 585/829 |
| 4,469,911 A | * | 9/1984 | Manning | 585/515 |
| 4,645,576 A | * | 2/1987 | Takezono et al. | 203/30 |
| 4,777,316 A | | 10/1988 | Harandi et al. | |
| 4,956,514 A | * | 9/1990 | Chu | 585/533 |
| 5,091,590 A | | 2/1992 | Harandi et al. | |
| 5,134,241 A | | 7/1992 | Le et al. | |
| 6,111,159 A | | 8/2000 | Huff et al. | |
| 6,518,473 B2 | | 2/2003 | Miller et al. | |
| 6,613,108 B1 | * | 9/2003 | Aittamaa et al. | 44/449 |
| 7,161,053 B2 | * | 1/2007 | Beckmann et al. | 585/530 |

(Continued)

FOREIGN PATENT DOCUMENTS

JP    H06(1994)-179630    6/1994
WO    WO 2009/055227    4/2009

OTHER PUBLICATIONS

Karinen, et al., "Reaction Equilibrium in the Isomerization of 2,4,4-Trimethyl Pentenes" in Ind. Eng. Chem. Res., 2001, 40, 1011-1015—month unknown.*

(Continued)

*Primary Examiner* — In Suk Bullock
*Assistant Examiner* — Bradley Etherton
(74) *Attorney, Agent, or Firm* — Kevin M. Faulkner

(57) ABSTRACT

Described is an apparatus for, and a method of, recovering linear butenes from a mixed feed comprising providing a first mixed feed comprising linear butenes and isobutene; contacting the first mixed feed with an oligomerization catalyst such as an MWW family zeolite in a first oligomerization reactor to produce a second mixed feed comprising the linear butenes, $C_8$ olefins and higher oligomers, and a reduced amount of isobutene relative to the first mixed feed; and separating the second mixed feed to produce a first effluent of first purified linear butenes, and a second effluent of $C_8$ olefins and higher oligomers. The oligomerization reactor may be a converted isobutene-to-methyl-t-butylether reactor.

11 Claims, 1 Drawing Sheet

(56) References Cited

U.S. PATENT DOCUMENTS

| | | |
|---|---|---|
| 7,183,450 B2 | 2/2007 | Brown et al. |
| 7,196,238 B2 | 3/2007 | Nurminen et al. |
| 7,473,812 B2 | 1/2009 | Peters et al. |
| 2002/0103406 A1 | 8/2002 | Mathys et al. |
| 2004/0030212 A1 | 2/2004 | Al-Soufi et al. |
| 2005/0043575 A1* | 2/2005 | Risch et al. .................. 585/324 |
| 2005/0121361 A1* | 6/2005 | Duplan et al. ................ 208/113 |
| 2006/0194998 A1* | 8/2006 | Umansky et al. ............ 585/467 |
| 2007/0185359 A1* | 8/2007 | Umansky et al. ............ 585/517 |
| 2007/0191662 A1* | 8/2007 | Oikarinen et al. ........... 585/533 |
| 2007/0213576 A1 | 9/2007 | Brown et al. |

OTHER PUBLICATIONS

Japanese Patent Office Dispatch No. 599080 (pp. 1-3)—dated Sep. 2013.
Japanese Patent Office Dispatch No. 184849 (pp. 1-4)—dated Mar. 2013.

\* cited by examiner

METHOD OF ISOLATING LINEAR BUTENES FROM A MIXED HYDROCARBON FEED

FIELD OF THE INVENTION

The present invention relates in general to an apparatus and method of removing isobutene from hydrocarbon feeds, and more particularly to the production/recovery of linear butenes, especially 1-butene, and $C_8$ olefins and higher oligomers.

BACKGROUND

Recovery of high purity 1-butene from refinery or chemical plant cracked $C_4$ streams, such as from a steam cracker or fluid catalytic cracker, requires that 1-butene be separated in high yield and high efficiency from all other species in the feed. Most species can be removed by fractionation. One of the difficulties in recovering linear butenes is that isobutene has a boiling point very close to that of the desired 1-butene. This makes isobutene very difficult to separate by fractionation. In light of this, a common method to remove isobutene from 1-butene feedstock is to convert the isobutene to methyl-t-butyl ether ("MTBE"). However, using MTBE as a gasoline additive is becoming less common, as regulations may phase out such production. Thus, other means for recovering linear butenes is needed.

It has been known to use certain catalysts to dimerize, oligomerize or otherwise convert olefins as in U.S. Pat. No. 3,531,539, U.S. Pat. No. 5,134,241, U.S. Pat. No. 6,518,473, U.S. Pat. No. 7,183,450, U.S. Pat. No. 7,196,238, US 2002/0103406, US 2004/0030212, and US 2007/0213576. Other olefin conversion processes are described in U.S. Pat. No. 4,777,316, U.S. Pat. No. 4,956,514, U.S. Pat. No. 6,111,159, and US 2007/0185359. What is needed is an industrially useful method of isolating and purifying linear butenes from hydrocarbon feeds containing linear butenes and isobutene. An apparatus that could utilize existing facilities designed and/or used for other purposes would be particularly useful.

SUMMARY OF THE INVENTION

Described herein is an apparatus for recovering linear butenes from a mixed feed comprising a polars-scrubber unit having an inlet and an outlet; a hydrogenation reactor having an inlet and an outlet, the hydrogenation reactor comprising a hydrogenation catalyst, wherein the hydrogenation reactor inlet is fluidly connected to the polars-scrubber outlet; a first oligomerization reactor having an inlet and outlet, the reactor inlet fluidly connected to the hydrogenation reactor outlet, the oligomerization reactor comprising an oligomerization catalyst, the catalyst allowing for gases and/or fluids to pass from the reactor inlet to the oligomerization reactor outlet, making reacting-contact with the catalyst there between; and a separating means having an inlet and an outlet, the separating means inlet fluidly connected to the oligomerization reactor outlet. In one embodiment, the apparatus derives from a converted MTBE production facility, wherein at least the MTBE reactor is converted to the oligomerization reactor by replacing the MTBE-producing catalyst with the oligomerization catalyst.

Also described is a method of recovering linear butenes from a mixed feed comprising providing a first mixed feed comprising linear butenes and isobutene; contacting the first mixed feed with an oligomerization catalyst in a first oligomerization reactor to produce a second mixed feed comprising the linear butenes, $C_8$ olefins and higher oligomers, and a reduced amount of isobutene relative to the first mixed feed; and separating the second mixed feed to produce a first effluent of first purified linear butenes, and a second effluent of $C_8$ olefins and higher oligomers. In one embodiment, the contacting takes place at a temperature of less than 105° C.

The various descriptive elements and numerical ranges disclosed herein can be combined with other descriptive elements and numerical ranges to describe preferred embodiments of the invention(s); further, any upper numerical limit of an element can be combined with any lower numerical limit of the same element to describe preferred embodiments.

DETAILED DESCRIPTION OF THE INVENTION

Figure 1:
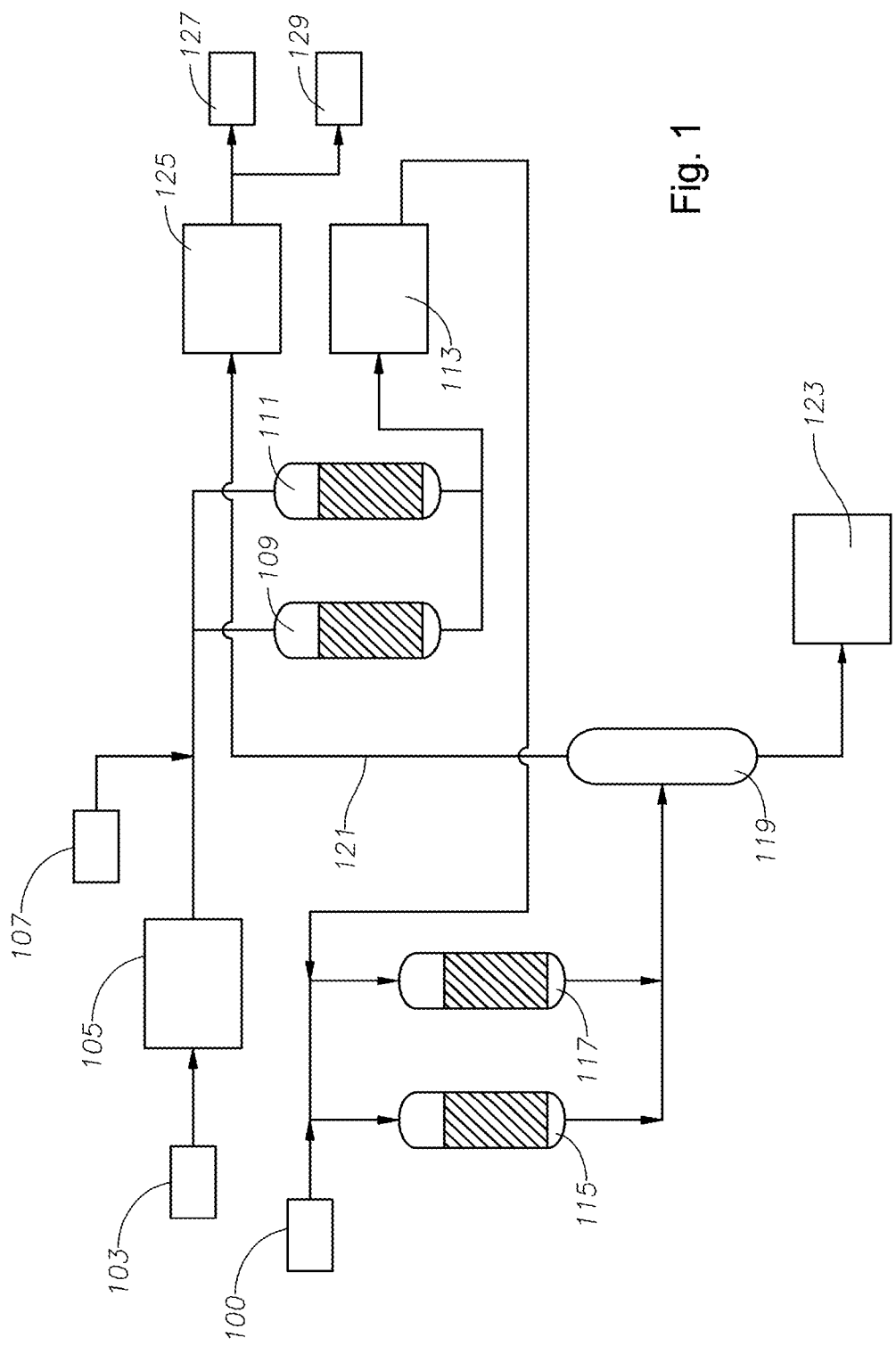
FIG. 1 is a schematic representation of one embodiment of an apparatus for recovering linear butenes from a hydrocarbon stream, one step of which is that of performing selective isobutene oligomerization and its isolation from unreacted hydrocarbons and reaction products.

Described herein is a method and apparatus for recovering linear butenes from a mixed hydrocarbon feed, characterized in that isobutene in the mixed hydrocarbon feed is selectively oligomerized to octenes and higher olefins using an oligomerization catalyst. Disclosed in a particular embodiment is a method of recovering (and/or producing) branched $C_8$ olefins; the term "recovering" meaning that the species being recovered is part of a mixture, and the term "producing" meaning that the species being recovered is formed from one or more components of a mixture. In certain embodiments described herein, the oligomerization catalyst is selected from the group consisting of MWW family zeolites, and mixtures thereof. The phrase "linear butenes" includes 1-butene and 2-butene; and "octenes" (or "$C_8$ olefins") include all isomers of olefins having eight carbon atoms including, but not limited to, 2,4,4-trimethyl-1-pentene, 2,4,4-trimethyl-2-pentene, 2,3,4-trimethyl-2-pentene, 2,3-dimethyl-2-hexene, and mixtures thereof.

The "mixed hydrocarbon feed" (or "mixed feed") may be so called raffinates (e.g., raff-1 and/or raff-2 feeds), and in certain embodiments comprises from 5 to 40 or 50 or 60 wt % isobutene, from 5 to 40 or 50 wt % 1-butene, from 5 to 30 or 40 or 50 wt % n-butane, from 5 to 30 or 40 or 50 wt % cis- and trans-2-butene, and from 1 to 10 or 20 wt % isobutane, each by weight of the mixed feed (100 wt %). The mixed feed may also have minor amounts (0.01 to 5 wt %) of polar molecules or molecules comprising polar moieties.

In one embodiment is a method of recovering linear butenes (or, alternately, branched $C_8$ olefins) from a mixed feed comprising providing a first mixed feed including at least linear butenes and isobutene, followed by contacting the first mixed feed with an oligomerization catalyst in a first oligomerization reactor to produce a second mixed feed comprising the linear butenes, $C_8$ olefins and higher oligomers, and a reduced amount of isobutene relative to the first mixed feed. The second mixed feed can then be subjected to a separation process through a separation means such as, for example, a fractionating means, to produce a first effluent of purified linear butenes, and a second effluent of $C_8$ olefins and higher oligomers.

In certain embodiments, the first mixed feed comprises from 5 or 10 or 20 wt % to 40 or 50 or 60 wt % isobutene, by weight of the first mixed feed.

In certain embodiments, a first mixed feed is provided additionally containing diolefins such as 1,3-butadiene. In such embodiments, the method of recovering linear butenes further comprises the step of hydrogenating the first mixed feed to produce a hydrogenated mixed feed comprising hydrogenated diolefins, linear butenes and isobutene. The hydrogenated mixed feed is subsequently contacted with an oligomerization catalyst in a first oligomerization reactor to produce a second mixed feed comprising the linear butenes, $C_8$ olefins and higher oligomers, the hydrogenated diolefins, and a reduced amount of isobutene relative to the first mixed feed. This second mixed feed can then be subjected to a separation process such as by fractionating the second mixed feed to produce a first effluent of purified linear butenes, and a second effluent of $C_8$ olefins and higher oligomers.

In certain embodiments, the purified linear butenes are further separated to provide a purified 1-butene stream. This separation step may take place using, for example, one or more fractionators as is commonly known in the art, or other means suitable for separating liquid and/or gaseous hydrocarbons into individual components. In certain embodiments, the second mixed feed is heated to within the range of from 50 to 200° C. before the separating step, and/or before the further (second) separation step.

In certain embodiments, sequential contacting steps are absent. More particularly, in certain embodiments the placement of sequential oligomerization reactors, where the reactant (e.g., first mixed feed) passes through one reactor, then another, is not used in the linear butene recovery method described herein. In certain embodiments, however, there are two or more oligomerization reactors present in the apparatus used to recover the linear butenes, those two or more reactors being parallel working reactors such that the reactant will be divided prior to entering the reactors then feed in such fashion to each reactor in parallel, or the reactant is fed to only one reactor, the other one or more reactors fluidly connected (but in isolation) for use when the oligomerization catalyst in the first reactor is being regenerated or replaced. Thus, in one embodiment is a second (or third, etc.) oligomerization reactor comprising oligomerization catalyst that is fluidly connected to a hydrogenation reactor and a separating means such as a fractionator, in parallel with the first oligomerization reactor but in fluid isolation therefrom until first use.

In certain embodiments, the first mixed feed is polars-scrubbed prior to hydrogenation. By "polars-scrubbed," what is meant is the first mixed feed is subjected to a process to remove polar molecules or molecules containing polar moieties such as alcohols, carboxylates, mercaptans, etc, or molecules containing heteroatoms (O, N, S, etc.) or any other species that may act as a catalyst poison. In one embodiment, the polars-scrubbing comprises contacting the first mixed feed with water in a water/feed contacting means, followed by contacting the first mixed feed with a drying means. In other embodiments, the first mixed feed is contacted with a mixture of water and other polar solvent such as an alcohol or ether in the water/feed contacting means. In the embodiments where the first mixed feed is polars-scrubbed, the scrubbed feed may be further subjected to a drying step to remove any water or water/solvent present in the feed. In one embodiment the scrubbed feed is passed through a drying means comprising a solid drying agent. In certain embodiments, the drying agent is selected from the group consisting of Group 1-2 metals, Group 1-2 sulfates, Group 1-2 hydrides, phosphorous pentoxide, alumina, alumina-silica, silica, activated carbon, molecular sieves, and mixtures thereof. The drying means may be physically removed from the water/feed contacting means, or may be located directly adjacent to one another.

In certain embodiments, there is no dehydrogenation step after the polars-scrubbing step. In other embodiments, there is no dehydrogenation step in any stage of the linear butene recovery described herein. By "dehydrogenation," what is meant is the removal of one or more hydrogen atoms from a hydrocarbon to form mono-olefins, di-olefins, etc.

The oligomerization reactor can operate under varying conditions of temperature, pressure and space velocity. The temperature of the reactants within the oligomerization reactor (or the "contacting temperature") can be maintained by any means known in the art such as water-jackets, etc. The pressure can be maintained by any means known in the art such as by pumps, etc. In certain embodiments, the first mixed feed is heated or cooled prior to entering the oligomerization reactor comprising the oligomerization catalyst. In one embodiment, the first mixed feed (or hydrogenated mixed feed) is at a temperature within the range of from 40 or 50 or 60° C. to 95 or 110 or 120 or 130 or 150° C. prior to the contacting in the oligomerization reactor. In certain embodiments, the contacting temperature in the first oligomerization reactor is maintained at a temperature at which the level of isobutene in the first effluent is less than 0.20 wt % by weight of the second mixed feed, and in particular embodiments the contacting temperature is within the range of from 40 or 50° C. to 95 or 100 or 105 or 110 or 120 or 150 or 200 or 250° C. In yet a more particular embodiment, the contacting temperature is less than 105 or 100 or 95° C. When referring to "oligomerization reactor temperature" what is meant is the temperature of the contents within the reactor, or, alternately, the "contacting temperature."

In certain embodiments, the first oligomerization reactor (or other parallel oligomerization reactors) operates at the minimum pressure at which all the components of the first mixed feed is a liquid at the desired temperature, and in particular embodiments is at a pressure within the range of from 1.0 or 1.1 or 1.2 MPa to 2 or 3 or 5 or 10 or 20 or 40 MPa.

In certain embodiments, the first oligomerization reactor (or other parallel oligomerization reactors) operates at the space velocity at which the level of isobutene in the first effluent is less than 0.20 wt % by weight of the second mixed feed, and in particular embodiments the reactor is operated at a space velocity within the range of from 2.0 or 2.5 or 3.0 to 5.0 or 6.5 or 7.0 or 9.0 or 10.0 or 11.0 or 12.0 ml feed/ml catalyst/hour. In other embodiments, the space velocity is less than 15 or 13 or 12 or 10 ml feed/ml catalyst/hour.

The oligomerization catalyst may lose efficiency over time. Thus, in certain embodiments, the contacting temperature of the first oligomerization reactor (as measured by the temperature of the reactants therein) is increased from a desirable minimum temperature at a rate within the range of from 1 or 2° C. to 8 or 10° C. per 100 hours (or 150 hours or 200 hours or 400 hours) of contacting up to a desirable upper temperature limit. The "desirable minimum temperature" in certain embodiments is a temperature within the range of from 40 to 60° C. A "desirable upper temperature limit" in certain embodiments is a temperature within the range of from 80° C. to 120° C. Upon reaching such a desirable upper temperature limit, the oligomerization catalyst may be subjected to a regeneration process, such as by contacting the catalyst with hydrogen gas, or replaced with fresh, catalyst. In certain embodiments, hydrogen gas is continually supplied (supplied during the simultaneous contacting of the catalyst with first mixed feed or first mixed hydrogenated feed) to the oligomerization reactor such that it contacts the oligomerization catalyst. In one embodiment, such additional contacting step includes hydrogen at a hydrogen-to-butadiene (molar) ratio within the range of from 1 or 5 to 30 or 50.

In certain embodiments, the oligomerization catalyst is selected from the group consisting of MWW family zeolites, and mixtures thereof. The term "MWW family zeolites" (or "material of the MWW family" or "molecular sieve of the MWW family"), as used herein, includes:
(i) molecular sieves made from a common first degree crystalline building block "unit cell having the MWW framework topology." A unit cell is a spatial arrangement of atoms which is tiled in three-dimensional space to describe the crystal as described in the ATLAS OF ZEOLITE FRAMEWORK TYPES (Ch. Baerlocher, L. B. McCusker & D. H. Olson 6$^{th}$ ed., 2007), the entire content of which is incorporated as reference;
(ii) molecular sieves made from a common second degree building block, a 2-dimensional tiling of such MWW framework type unit cells, forming a "monolayer of one unit cell thickness," preferably one c-unit cell thickness;
(iii) molecular sieves made from common second degree building blocks, "layers of one or more than one unit cell thickness," wherein the layer of more than one unit cell thickness is made from stacking, packing, or binding at least two monolayers of one unit cell thick of unit cells having the MWW framework topology. The stacking of such second degree building blocks can be in a regular fashion, an irregular fashion, a random fashion, or any combination thereof, or
(iv) molecular sieves made by any regular or random 2-dimensional or 3-dimensional combination of unit cells having the MWW framework topology.

The MWW family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize the molecular sieve are obtained by standard techniques using the K-alpha doublet of copper as the incident radiation and a diffractometer equipped with a scintillation counter and associated computer as the collection system. Materials belonging to the MWW family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in EP 0293032), ITQ-1 (described in U.S. Pat. No. 6,077,498), ITQ-2 (described in WO 97/17290), ITQ-30 (described in WO 2005118476), MCM-36 (described in U.S. Pat. No. 5,250,277), MCM-49 (described in U.S. Pat. No. 5,236,575), UZM-8 (described in U.S. Pat. No. 6,756,030), and MCM-56 (described in U.S. Pat. No. 5,362,697). The entire contents of these patents are incorporated herein by reference. In a particular embodiment, the oligomerization catalyst consists essentially of MCM-22 (meaning a filler or binder may be present) or comprises MCM-22 in another embodiment. In another particular embodiment, the oligomerization catalyst consists essentially of MCM-49 (meaning a filler or binder may be present) or comprises MCM-49 in another embodiment.

It is to be appreciated that the MWW family zeolites described above are distinguished from conventional large pore zeolite alkylation catalysts, such as mordenite, in that the MWW materials have 12-ring surface pockets which do not communicate with the 10-ring internal pore system of the molecular sieve.

The zeolitic materials designated by the IZA-SC as being of the MWW topology are multi-layered materials which have two pore systems arising from the presence of both 10 and 12 membered rings. The ATLAS OF ZEOLITE FRAMEWORK TYPES classes five differently named materials as having this same topology: MCM-22, ERB-1, ITQ-1, PSH-3, and SSZ-25.

It will be understood by a person skilled in the art that the MWW family material may contain impurities, such as amorphous materials; unit cells having non-MWW framework topologies (e.g., MFI, MTW); and/or other impurities (e.g., heavy metals and/or organic hydrocarbons). Typical examples of the non-MWW family molecular sieve(s) co-existing with the MWW family molecular sieve(s) of this disclosure are Kenyaite, EU-1, ZSM-50, ZSM-12, ZSM-48, ZSM-5, Ferrierite, Mordenite, Sodalite, and/or Analcine. Other examples of the non-MWW family molecular sieve(s) co-existing with the MWW family molecular sieve(s) of this disclosure are molecular sieves having framework type of EUO, MTW, FER, MOR, SOD, ANA, and/or MFI. The MWW family materials of this disclosure are preferably substantially free of non-MWW family material(s). The term "substantially free of non-MWW family material(s)" used herein means the MWW family material of this disclosure preferably contains less than 50 wt %, preferably less than 20 wt %, of non-MWW family materials in the MWW family materials, which weight percent (wt %) values are based on the combined weight of impurities and pure phase MWW family materials.

The MWW family zeolites can take on any physical form as the, or part of the, "oligomerization catalyst" suitable for contacting with the first mixed feed (or first mixed hydrogenated feed and/or first mixed scrubbed feed). The MWW family zeolites can be shaped into a wide variety of particle sizes. In certain embodiments, the particles can be in the form of a powder, a granule, or a molded product such as an extrudate having a particle size sufficient to pass through a 2 mesh (Tyler) screen and be retained on a 400 mesh (Tyler) screen (0.037 mm opening). In cases where the catalyst is molded, such as by extrusion, the crystals can be extruded before drying or partially dried and then extruded. In certain embodiments, the oligomerization catalyst comprises MWW family zeolites and from 0 or 0.1 or 5 or 10 or 20 wt % to 40 or 50 or 60 or 80 wt % binder, by weight of the catalyst and binder. Any suitable binder as is known in the art may be used, such as natural or synthetic clays, and more particularly, silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia. It may also be advantageous to provide at least a part of the foregoing matrix materials in colloidal form so as to facilitate extrusion of the bound catalyst component(s). In one embodiment, the oligomerization catalyst is in the form of 0.2 or 0.5 to 3 or 5 or 8 mm diameter extrudate. The bulk density of the oligomerization catalyst is within the range of from a lower limit of 0.400 or 0.410 or 0.415 to an upper limit of 0.490 or 0.500 or 0.510 g/cm$^3$ in certain embodiments.

In certain embodiments, the step of contacting the oligomerization catalyst with the mixed feed also includes contacting hydrogen at least every 500 hours of run time for a time of at least 1 hour during continuous run. In one embodiment, such additional contacting step includes hydrogen at a hydrogen-to-butadiene molar ratio within the range of from 1 or 5 to 30 or 50.

The oligomerization catalyst may be replaced at any time to maintain optimal conversion and economics. In certain embodiments a step of replacing the oligomerization catalyst occurs at a rate of less than or equal to one time per week, and less than one time per month in another embodiment, and less than one time in two months in yet another embodiment, and less than one time in five months in yet another embodiment.

Referring back to the optional hydrogenation step, the hydrogenating step may include in certain embodiments contacting the first mixed feed with a hydrogenation catalyst and hydrogen in a hydrogenation reactor, where the reactor is maintained at a temperature within the range of from 10 or 20° C. to 120 or 150° C. When present, the hydrogenation catalyst comprises a metal selected from the group consisting of Group 8 to Group 11 metals, and mixtures thereof, in certain embodiments. In another embodiment, the hydrogenation catalyst comprises a metal selected from the group consisting of Group 9 to Group 10 metals, and mixtures thereof. Hydrogen is provided to the hydrogenation reactor by any suitable means, and in certain embodiments is provided in an amount such that the hydrogen-to-butadiene molar ratio is within the range of from 0.2 or 0.5 or 1 to 5 or 8 or 10. In certain embodiments, the hydrogenation catalyst is contacted with a natural (or regen) gas stream to regenerate the hydrogenation catalyst.

The desired product, linear butenes, and in particular, 1-butene can be isolated from the first effluent at a desirably high concentration. In one embodiment, the first purified 1-butene effluent ("first effluent") comprises less than 0.40 or 0.30 or 0.20 or 0.10 wt % isobutene, by weight of the first effluent. In another embodiment, the second mixed feed comprises less than 0.40 or 0.30 or 0.20 or 0.10 wt % isobutene, by weight of the second mixed feed.

In another embodiment is an apparatus for recovering linear butenes from a mixed hydrocarbon feed. The apparatus is consistent with carrying out the methods as described herein in its various embodiments. The apparatus may be constructed as an original unit, or constructed by converting some other type of unit such as by converting a MTBE-production unit to the apparatus described herein. Thus, in certain embodiments, prior to providing the first mixed feed, a reactor comprising an ether-conversion catalyst used to convert isobutene to an ether compound is converted into at least the first oligomerization reactor by at least replacing the ether-conversion catalyst with the oligomerization catalyst. Stated another way, the oligomerization reactor is a converted isobutene-to-methyl-t-butyl ether ("MTBE") reactor in a particular embodiment, "converted" meaning that the basic structure of the reactor is maintained but the reactor interior is adapted for the use of the oligomerization catalyst for the purpose stated herein.

A more particular embodiment is an apparatus for recovering linear butenes from a mixed feed comprising at least one polars-scrubber unit having an inlet and an outlet; a hydrogenation reactor having an inlet and an outlet, the hydrogenation reactor comprising a hydrogenation catalyst, wherein the hydrogenation reactor inlet is fluidly connected to the polars-scrubber outlet; a first oligomerization reactor having an inlet and outlet, the reactor inlet fluidly connected to the hydrogenation reactor outlet, the oligomerization reactor comprising an oligomerization catalyst, the catalyst allowing for gases and/or fluids to pass from the reactor inlet to the oligomerization reactor outlet, making reacting-contact with the catalyst there between; and a separating means having an inlet and an outlet, the separating means inlet fluidly connected to the oligomerization reactor outlet. In other embodiments, there may be more than one inlet and outlet in each part of the apparatus. In certain embodiments, the "fluid connection" is through a conduit (or other means suitable for transporting gases and/or liquids) between the outlet of one part and the inlet of another part. The apparatus may be originally built, partially originally built, or derived completely from pre-existing reactors and fluid connections.

In certain embodiments, the hydrogenation reactor also comprises a natural gas inlet (and outlet for reacted gas), allowing for the regeneration of the hydrogenation catalyst.

In certain embodiments, there is no need for a hydrogenation step, thus, the apparatus may further comprise an alternate bypass fluid connection from the polars-scrubber to the oligomerization reactor, thus allowing the scrubbed mixed feed to enter directly into the oligomerization reactor. In any case, the polars-scrubber unit comprises a wash means and a drying means in certain embodiments, wherein the drying means comprising a drying agent. During operation, the polars-scrubbing unit also comprises a mixed feed comprising diolefins, linear butenes and optionally isobutene.

There is at least one oligomerization reactor, and each reactor may be operated independent of the other. The oligomerization reactor may take on any suitable form, preferably such that allows for optimal contacting between the oligomerization catalyst and scrubbed mixed feed. In certain embodiments, the first oligomerization reactor (or other oligomerization reactors) is a tubular reactor comprising a plurality of tubes associated with a heat transfer means. The plurality of tubes typically run parallel to one another and allow for heat transfer by providing a continuous flow of fluid such as water (at a desirable temperature) around the tubes. The tubes are maintained at a temperature that will maintain the catalyst and reactants within at the desired temperature as described above. In any case, the oligomerization catalyst is placed in the oligomerization reactor as a fluidizable bed in certain embodiments, or as a porous solid allowing gas/fluid to flow there through in another embodiment. During operation of the apparatus, the oligomerization reactor also comprises linear butenes, $C_8$ olefins and higher oligomers.

As stated above, there may be more than one oligomerization reactor in parallel or series, preferably in parallel. The second or third or more oligomerization reactor may operate simultaneously with the first oligomerization reactor, or alternately. In certain embodiments, a second oligomerization reactor comprising oligomerization catalyst is fluidly connected to the hydrogenation reactor (or bypassed from the polars-scrubber to the oligomerization reactor) and the fractionation (separating) unit, in parallel with the first oligomerization reactor but in fluid isolation therefrom until first use. In this manner, fresh oligomerization catalyst can be provided without shutting down the unit.

To allow for in situ regeneration of the oligomerization catalyst, the oligomerization reactor further comprises a hydrogen gas inlet in certain embodiments. The hydrogen gas may be supplied to the reactor continuously during oligomerization operations, or when the reactor is in isolation from the first mixed feed.

The fluid connections to and from the oligomerization reactor may be provided with temperature control means (heating and/or cooling means). In one embodiment, a cooling means is provided for the fluid connection between the hydrogenation reactor and the oligomerization reactor. In another embodiment, a heating means is provided for the fluid connection between the oligomerization reactor and the separation means.

A specific embodiment of the apparatus is described with reference to FIG. 1. The first mixed feed 103 comprising linear butenes is fed to a polars-scrubber 105, which comprises a washing means. The washing means subjects the first mixed feed 103 to a step of intimately contacting the feed with water and/or a polar solvent, followed by passing the feed 103 through a drying means, in one embodiment a first drying means 109 and/or a second drying means 111. The scrubbed mixed feed is then transferred through a fluid connection to a hydrogenation reactor 113. Alternately, the scrubbed feed is transferred directly to a first oligomerization reactor 115 and/or a second oligomerization reactor 117 through a fluid connection that by-passes the hydrogenation reactor.

The resulting second mixed feed is then transferred through a fluid connection to a first separation means 119 such as a fractionation unit. After being subjected to a separation process within the first separation means 119, a second effluent of $C_8$ olefins and higher oligomers is obtained where it can be stored in 123 and/or used directly as an additive to enrich a gasoline mixture with higher levels of octane. A first effluent of first purified linear butenes 121 is then transferred through a fluid connection to a second separation means 125, where a purified 1-butene stream 127 is isolated, and inert hydrocarbons 129 are recovered.

An exemplary flow scheme of reactants and products in the methods described herein, in order, is (1) first mixed feed, (2) optional scrubbed mixed feed, (3) optional hydrogenated mixed feed, (4) second mixed feed, (5) first effluent (including the linear butenes) and (6) second effluent ("bottoms", including $C_8$ olefins and higher oligomers). The first effluent can be separated further into (7) a purified 1-butene stream and (8) 2-butenes (and other "inert hydrocarbons"). By "inert hydrocarbon," what is meant are hydrocarbons not reactive to the oligomerization catalyst below 100° C.

Thus, in a particular embodiment the apparatus for recovering linear butenes from a mixed feed comprises a polarsscrubber unit having an inlet and an outlet; a hydrogenation reactor having an inlet and an outlet, the hydrogenation reactor comprising a hydrogenation catalyst, wherein the hydrogenation reactor inlet is fluidly connected to the polars-scrubber outlet; a first oligomerization reactor having an inlet and outlet, the reactor inlet fluidly connected to the hydrogenation reactor outlet, the oligomerization reactor comprising an oligomerization catalyst, the catalyst allowing for gases and/or fluids to pass from the reactor inlet to the oligomerization reactor outlet, making reacting-contact with the catalyst there between; and a separating means having an inlet and an outlet, the separating means inlet fluidly connected to the oligomerization reactor outlet. The flow of hydrocarbon feed into the inlet of the polars-scrubber unit through the apparatus is preferably continuous, wherein the feed is scrubbed, followed by being dried, the feed then leaving the outlet of the scrubber (or drying sub-unit) to enter the hydrogenation reactor in one embodiment. In certain embodiments, the hydrogenation reactor may not be active (such as not being heated and/or not exposed to hydrogen gas) yet allowing feed to flow through. In another embodiment, the hydrogenation reactor is bypassed through a fluid connection from the outlet of the scrubber to the inlet of the oligomerization reactor. In any case, the feed then flows into the oligomerization reactor inlet from the hydrogenation reactor outlet. The feed then contacts the catalyst within the oligomerization reactor and the reaction product leaves the oligomerization reactor outlet to enter the separating means through the inlet of the separating means. In any case, there may be more than one inlet and more than one outlet in each unit.

In one embodiment, an inert hydrocarbon recycle feed 100 is provided, and in yet another embodiment an inert hydrocarbon start-up feed 107 is also provided, either or both of which may be run continuously to provide inert hydrocarbons, or only upon startup of a new oligomerization catalyst in either or all of a first oligomerization reactor, second oligomerization reactor, etc.

Provided in a particular embodiment is a method of recovering linear butenes from a mixed feed comprising providing a first mixed feed comprising linear butenes and less than 40 wt %, by weight of the first mixed feed, of isobutene; contacting the first mixed feed with an MWW family zeolite oligomerization catalyst in a first oligomerization reactor to produce a second mixed feed comprising the linear butenes, $C_8$ olefins and higher oligomers, and a reduced amount of isobutene relative to the first mixed feed, wherein the contacting takes place at a temperature within the range of from 40 to 105° C. and at a space velocity within the range of from 8.0 to 2.0 ml feed/ml catalyst/hr; and separating the second mixed feed to produce a first effluent of first purified linear butenes, and a second effluent of $C_8$ olefins and higher oligomers.

In yet another embodiment is a method for recovering and/or producing branched $C_8$ olefins, comprising providing a first mixed feed comprising linear butenes and isobutene; contacting the first mixed feed with an oligomerization catalyst in a first oligomerization reactor to produce a second mixed feed comprising the linear butenes, $C_8$ olefins and higher oligomers, and a reduced amount of isobutene relative to the first mixed feed; and separating the second mixed feed to produce a first effluent of first purified linear butenes, and a second effluent of $C_8$ olefins and higher oligomers, wherein there is greater than 30 wt %, by weight of the second effluent, of 2,4,4-trimethyl-1-pentene in the second effluent. By "branched $C_8$ olefins," what is meant are olefins that comprise 8 carbon atoms, wherein there is at least one secondary carbon (a carbon having three other carbon atoms bound to it), and optionally at least one tertiary carbon. In another embodiment, the ratio of 2,4,4-trimethyl-1-pentene to 2,4,4-trimethyl-2-pentene in the second effluent decreases within the range from 12.0 to 3.0 when (i) the contacting temperature within the first oligomerization reactor increases within the range from 50° C. to 105° C., (ii) the space velocity decreases within the range from 12 ml feed/ml catalyst/hour to 2 ml feed/ml catalyst/hour, or (iii) both. A hydrogenation reaction step may also be present, and the oligomerization reactor temperature, velocity, and other parameters can be varied as described herein. When stating "within the range from," what is meant in this embodiment is that, for example, the ratio may decrease from a high value of 8.1 to a low value of 4.2 when the temperature is increased from 61 to 93° C., and/or the space velocity is decreased from 11.2 to 5.7 ml/ml/hr, or any other upper and lower value within the ranges.

In another embodiment, there is greater than 40 wt %, by weight of the second mixed feed, of 2,4,4-trimethyl-1-pentene in the second effluent, and within the range of from 30 or 40 or 50 to 70 or 80 or 90 wt %, by weight of the second effluent in other embodiments. The amount of 2,4,4-trimethyl-1-pentene can be increased with a decrease in the oligomerization reactor temperature and/or an increase of the space velocity, as described above.

In certain embodiments, the apparatus is built from an existing unit used for other purposes, meaning in one embodiment that no new reactors are built to accommodate the apparatus. Recovery of high purity 1-butene from refinery or chemical plant cracked $C_4$ streams, such as from a steam cracker or fluid catalytic cracker, requires that 1-butene be separated in high yield and high efficiency from all other species in the feed. Most species can be removed by fractionation. However, isobutene is very difficult to separate by fractionation. A common method to remove isobutene from 1-butene feedstock is to convert the isobutene to MTBE. This can be done in a two-stage process, in which:

The feed is mixed with a limited amount of methanol and reacted over resin catalyst to convert up to about 95% of the feed to isobutene. Up to three or more reactors can be used in a first stage, two parallel tubular reactors followed by one fixed bed reactor in certain designs;

Separating the MTBE product from the $C_4$ feed;

Mixing the remaining unreacted feed with a large excess of methanol in a second stage single fixed bed reactor to achieve an overall conversion of at least 99.5%; and Separating the remaining unreacted feed for further purification of 1-butene.

The apparatus described herein may be built by retrofitting, for example, existing MTBE units to produce high octane Mogas blending or specialty chemical components with minimal unit upgrades and/or modifications. In one embodiment, no new reactor is built or provided to the apparatus described herein.

MWW zeolite catalyst can be used as a catalyst for dimerizing/oligomerizing olefins, including $C_4$ olefins. These catalysts convert isobutene to octenes and heavier oligomers at advantageously low temperatures, allowing them to be easily fractionated away from the 1-butene feedstock. The required isobutene conversion may be achieved in just one reactor at temperatures and pressures within the vessel designs (designed for other uses such as MTBE production). This allows a second tubular reactor to be used as a spare reactor to allow a rapid transition to a new bed of catalyst when the catalyst in use becomes spent.

Feed to the oligomerization catalyst is preferably dried to prevent water from inhibiting the desired conversion. In the case of a retrofit, two idled fixed bed reactors can be converted to driers and reconfigured upstream of the oligomerization reactor(s). Since the oligomerization reactor operates at higher pressure than a MTBE synthesis reactor, it needs higher pressure feed pumps. These can be provided by configuring the selective diolefin saturator equipment, which typically operates at even higher pressure, upstream of the dimerization reactor.

Reusing the equipment as described above limits the retrofit changes to piping changes and, possibly, a minor upgrade of the heat source for the debutanizer tower to achieve satisfactory removal of $C_4$ from the $C_8$ olefins and higher oligomers. Any remaining idle fractionation towers, such as a second debutanizer and/or a methanol-water separation tower, can be reused to further fractionate the dimer/oligomer product into three fractions:

Recover the remaining $C_4$ components to maximize 1-butene recovery;

A light naphtha stream suitable for motor gasoline blending or specialty chemical end uses; and/or A heavy naphtha stream suitable for diesel blending or specialty chemical end uses.

The following is a non-limiting example of embodiments of the invention.

EXAMPLES

The apparatus and methods were tested in a demonstration pilot-scale plant using about 80 ml of MCM-22 oligomerization catalyst (65 wt % zeolite with 35 wt % alumina binder, $\frac{1}{16}$ inch diameter cylindrical extrudate, having a bulk density of from 0.416-0.497 $g/cm^3$, available from ExxonMobil Chemical Co., Houston Tex.) in an oligomerization reactor volume of about 250 ml. The "feeds" or "mixed feeds" in Table 1 are an average of 10 cylinders of steam cracked $C_4$s, all having been water-scrubbed and dried to remove polar impurities. The mixed feeds in Table 1 were passed through the oligomerization reactor only once at the indicated rate (ml/hr), and all of feeds A through F were run over a period of about 5 months. The data in Table 2 are representative samples from those runs. The pressure in the oligomerization reactor was about 1.55 MPa, the oligomerization reactor temperature and space velocity varied as indicated in the Table 2. The amounts of isobutene and the $C_8$ and higher oligomers ("$C_8$+") are those in the reaction product from the oligomerization reactor ("second mixed feed"), and were normalized against the measured amounts of components that are non-reactive with the oligomerization catalyst MCM-22 that were measured before and after the reaction. An indication of "yes" under "DIOS" means that a selective diolefins hydrogenator was used, typically at a temperature within the range of about 44-57° C. under flow of hydrogen gas. Table 3 summarizes the $C_8$ and higher oligomers compositions for three representative samples acquired under different conditions.

TABLE 1

Mixed Feed Compositions

| Component | Feed A | Feed B | Feed C | Feed D | Feed E | Feed F |
|---|---|---|---|---|---|---|
| i-butane | 2.9423 | 5.3180 | 4.2352 | 6.4693 | 7.0693 | 6.2825 |
| i-butene | 27.9032 | 33.4577 | 32.7363 | 34.1978 | 29.4108 | 30.6018 |
| 1-butene | 26.8029 | 23.7748 | 26.8046 | 23.7737 | 25.3130 | 26.6140 |
| 1,3-butadiene | 0.1337 | 0.1660 | 0.1846 | 0.1750 | 0.1732 | 0.2140 |
| n-butane | 23.6995 | 18.6358 | 15.1489 | 15.5295 | 16.9812 | 15.1900 |
| t-2-butene | 10.7245 | 10.6429 | 11.7044 | 10.9191 | 11.5565 | 12.2375 |
| c-2-butene | 7.3578 | 7.5379 | 8.8536 | 7.8099 | 8.3859 | 8.0914 |
| Other | 0.4128 | 0.4668 | 0.3325 | 1.1256 | 1.1101 | 0.7689 |

TABLE 2

Representative Oligomerization Results

| Time, days | DIOS | Feed Rate, ml/hr | Temp, ° C. | Space Velocity, ml/ml/hr | isobutene, wt % | $C_8$+, wt % (of second mixed feed) |
|---|---|---|---|---|---|---|
| 1 | No | 421 | 52 | 5.26 | <0.001 | 35.16 |
| 3 | No | 427 | 61 | 5.34 | <0.001 | 33.69 |
| 19 | No | 911 | 61 | 11.39 | 1.359 | 30.92 |
| 22 | No | 900 | 61 | 11.24 | 2.394 | 28.03 |
| 30 | No | 489 | 72 | 6.12 | 0.298 | 32.91 |
| 45 | No | 495 | 77 | 6.18 | 0.906 | 34.31 |
| 51 | No | 486 | 82 | 6.07 | 0.493 | 36.15 |
| 53 | No | 470 | 93 | 5.88 | 0.119 | 37.21 |
| 56 | No | 434 | 93 | 5.43 | 0.019 | 38.37 |
| 91 | Yes | 491 | 93 | 6.23 | 0.086 | 37.30 |
| 93 | Yes | 495 | 93 | 6.19 | 0.018 | 46.02 |
| 95 | Yes | 440 | 93 | 5.50 | 0.017 | 47.18 |
| 96 | Yes | — | 94 | 6.26 | 0.041 | 44.44 |
| 98 | No | 441 | 93 | 5.52 | 0.039 | 40.71 |
| 102 | Yes | 503 | 93 | 6.28 | 0.037 | 40.85 |
| 110 | No | 494 | 71 | 6.18 | 0.263 | 32.41 |
| 115 | Yes | 505 | 88 | 6.31 | 0.143 | 32.24 |
| 120 | Yes | 241 | 93 | 3.01 | 0.028 | 37.14 |
| 122 | Yes | 235 | 93 | 2.94 | 0.026 | 37.36 |
| 131 | Yes | 236 | 93 | 2.96 | 0.029 | 36.17 |

TABLE 3

Representative $C_8$ olefins and higher oligomer compositions

| | Time, days | | |
|---|---|---|---|
| | 48 | 21.5 | 104 |
| DIOS | No | No | No |
| Feed rate, ml/hr | 498 | 916 | 499 |
| Temp, ° C. | 60 | 60 | 93 |
| Space Velocity, ml/ml/hr | 6.22 | 11.45 | 6.24 |
| Isobutene conversion, % | 78.8 | 92.0 | 99.8 |

TABLE 3-continued

Representative C$_8$ olefins and higher oligomer compositions

| | Time, days | | |
|---|---|---|---|
| | 48 | 21.5 | 104 |
| weight percent components (of C$_8$+ products): | | | |
| C$_8$ content | 87.2 | 79.7 | 73.7 |
| C$_{12}$ content | 10.8 | 16.1 | 20.0 |
| C$_{18}$+ content | 2.02 | 4.2 | 6.3 |
| weight percent particular components (of C$_8$ and C$_{12}$ products): | | | |
| 2,4,4-trimethyl-1-pentene | 74.9 | 54.7 | 37.2 |
| 2,4,4-trimethyl-2-pentene | 6.5 | 9.5 | 11.4 |
| 2,3,4-trimethyl-2-pentene | 0.3 | — | 4.8 |
| 2,3-dimethyl-2-hexene | 0.2 | — | 1.6 |
| Other C$_8$s | 5.3 | 15.3 | 18.8 |
| 2,2,4,6,6-pentamethyl heptene | 1.8 | 3.7 | 6.8 |
| Other C$_{12}$s | 9.0 | 12.4 | 13.2 |

Having described the various elements of the apparatus and methods, described herein in numbered embodiments is:

1. An apparatus for recovering linear butenes from a mixed feed comprising (or "consisting essentially of" in another embodiment):
   a polars-scrubber unit having an inlet and an outlet;
   a hydrogenation reactor having an inlet and an outlet, the hydrogenation reactor comprising a hydrogenation catalyst, wherein the hydrogenation reactor inlet is fluidly connected to the polars-scrubber outlet;
   a first oligomerization reactor having an inlet and outlet, the reactor inlet fluidly connected to the hydrogenation reactor outlet, the oligomerization reactor comprising an oligomerization catalyst, the catalyst allowing for gases and/or fluids to pass from the reactor inlet to the oligomerization reactor outlet, making reacting-contact with the catalyst there between; and
   a separating means having an inlet and an outlet, the separating means inlet fluidly connected to the oligomerization reactor outlet.

2. The apparatus of numbered embodiment 1, further comprising providing an alternate bypass fluid connection from the polars-scrubber to the oligomerization reactor.

3. The apparatus of numbered embodiments 1 and 2, wherein the first oligomerization reactor is a tubular reactor comprising a plurality of tubes associated with a heat transfer means.

4. The apparatus of any of the previously numbered embodiments, wherein the hydrogenation catalyst comprises a metal selected from the group consisting of Group 8 to Group 11 metals, and mixtures thereof.

5. The apparatus of any of the previously numbered embodiments, wherein the oligomerization catalyst is selected from the group consisting of MWW family zeolites, and mixtures thereof.

6. The apparatus of any of the previously numbered embodiments, wherein a cooling means is provided for the fluid connection between the hydrogenation reactor and the oligomerization reactor.

7. The apparatus of any of the previously numbered embodiments, wherein a heating means is provided for the fluid connection between the oligomerization reactor and the separating means.

8. The apparatus of any of the previously numbered embodiments, wherein the polars-scrubber unit comprises a wash means and a drying means, the drying means comprising a drying agent.

9. The apparatus of any of the previously numbered embodiments, wherein the oligomerization reactor is a converted isobutene-to-methyl-t-butylether reactor.

10. The apparatus of any of the previously numbered embodiments, wherein a second oligomerization reactor comprising oligomerization catalyst is fluidly connected to the hydrogenation reactor and the separating means, in parallel with the first oligomerization reactor but in fluid isolation therefrom until first use.

11. A method of recovering linear butenes from a mixed feed comprising: providing a first mixed feed comprising linear butenes and isobutene;
    contacting the first mixed feed with an oligomerization catalyst in a first oligomerization reactor to produce a second mixed feed comprising the linear butenes, C$_8$ olefins and higher oligomers, and a reduced amount of isobutene relative to the first mixed feed; and
    separating the second mixed feed to produce a first effluent of first purified linear butenes, and a second effluent of C$_8$ olefins and higher oligomers.

12. The method of numbered embodiment 11:
    the first mixed feed additionally containing diolefins;
    hydrogenating the first mixed feed to produce a hydrogenated mixed feed comprising hydrogenated diolefins, linear butenes and isobutene;
    contacting the hydrogenated mixed feed with an oligomerization catalyst in a first oligomerization reactor to produce a second mixed feed comprising the linear butenes, C$_8$ olefins and higher oligomers, and the hydrogenated diolefins and a reduced amount of isobutene relative to the first mixed feed; and
    separating the second mixed feed to produce a first effluent of purified linear butenes, and a second effluent of C$_8$ olefins and higher oligomers.

13. The method of numbered embodiments 11 and 12, wherein the purified linear butenes are further separated to provide a purified 1-butene stream.

14. The method of any of the previously numbered embodiments 11-13, wherein the first mixed feed is polars-scrubbed prior to contacting (or hydrogenation in certain embodiments).

15. The method of any of the previously numbered embodiments 11-14, wherein there is no dehydrogenation step after the polars-scrubbing step.

16. The method of any of the previously numbered embodiments 11-15, wherein polars-scrubbing comprises contacting the first mixed feed with water, followed by contacting the first mixed feed with a drying agent.

17. The method of any of the previously numbered embodiments 11-16, wherein the first mixed feed (or hydrogenated mixed feed) is at a temperature within the range of from 50 to 150° C. prior to the contacting in the oligomerization reactor.

18. The method of any of the previously numbered embodiments 11-17, wherein the first oligomerization reactor operates at a pressure within the range of from 1.0 to 40 MPa.

19. The method of any of the previously numbered embodiments 11-18, wherein the first oligomerization reactor temperature is increased from a desirable minimum temperature at a rate within the range of from 1 to 10° C. per 100 hours of contacting up to a desirable upper temperature limit.

20. The method of any of the previously numbered embodiments 11-19, wherein the contacting in the first oligomerization reactor takes place at a temperature within the range of from 40 to 105° C.

21. The method of any of the previously numbered embodiments 11-20, wherein the oligomerization catalyst is selected from the group consisting of MWW family zeolites, and mixtures thereof.
22. The method of any of the previously numbered embodiments 11-21, wherein the hydrogenation catalyst comprises a metal selected from the group consisting of Group 8 to Group 11 metals, and mixtures thereof.
23. The method of any of the previously numbered embodiments 11-22, wherein butadiene is present in the first mixed feed, and the hydrogen-to-butadiene molar ratio is within the range of from 0.2 to 10.
24. The method of any of the previously numbered embodiments 11-23, wherein the contacting also includes hydrogen at least every 500 hours of run time for a time of at least 1 hour during continuous run.
25. The method of any of the previously numbered embodiments 11-24, wherein the contacting also includes hydrogen at a hydrogen-to-butadiene molar ratio within the range of from 1 to 50.
26. The method of any of the previously numbered embodiments 11-25, wherein the first purified 1-butene effluent comprises less than 0.20 wt % isobutene.
27. The method of any of the previously numbered embodiments 11-26, wherein the first mixed feed comprises from 5 to 60 wt % isobutene.
28. The method of any of the previously numbered embodiments 11-27, wherein a second oligomerization reactor comprising oligomerization catalyst is fluidly connected to a hydrogenation reactor and a separating unit, in parallel with the first oligomerization reactor but in fluid isolation therefrom until first use.
29. The method of any of the previously numbered embodiments 11-28, wherein the space time velocity in the first oligomerization reactor is less than 15 ml feed/ml catalyst/hour and the contacting takes place at a temperature of less than 100 or 105° C.
30. The method of any of the previously numbered embodiments 11-29, wherein there is less than 0.20 wt %, by weight of the second mixed feed, of isobutene in the first effluent.
31. The method of any of the previously numbered embodiments 11-30, wherein there is greater than 30 wt %, by weight of the second mixed feed, of 2,4,4-trimethyl-1-pentene in the second effluent.
32. The method of any of the previously numbered embodiments 11-31, wherein the space time velocity in the first oligomerization reactor is within the range of from 2 ml feed/ml catalyst/hour to 12 ml feed/ml catalyst/hour.
33. The method of any of the previously numbered embodiments 11-32, wherein the contacting within the first oligomerization reactor takes place at a temperature within the range of from 40° C. to 95 or 105° C.
34. The method of any of the previously numbered embodiments 11-33, wherein the ratio of 2,4,4-trimethyl-1-pentene to 2,4,4-trimethyl-2-pentene in the second effluent decreases within the range of from 12.0 to 3.0 when (i) the contacting temperature within the first oligomerization reactor increases within the range from 50° C. to 95 or 105° C., (ii) the space velocity decreases within the range from 12 ml feed/ml catalyst/hour to 2 ml feed/ml catalyst/hour, or (iii) both.

In yet another embodiment is the use of an apparatus for recovering linear butenes from a mixed feed comprising a polars-scrubber unit having an inlet and an outlet; a hydrogenation reactor having an inlet and an outlet, the hydrogenation reactor comprising a hydrogenation catalyst, wherein the hydrogenation reactor inlet is fluidly connected to the polars-scrubber outlet;

a first oligomerization reactor having an inlet and outlet, the reactor inlet fluidly connected to the hydrogenation reactor outlet, the oligomerization reactor comprising an oligomerization catalyst, the catalyst allowing for gases and/or fluids to pass from the reactor inlet to the oligomerization reactor outlet, making reacting-contact with the catalyst there between; and a separating means having an inlet and an outlet, the separating means inlet fluidly connected to the oligomerization reactor outlet. Various aspects of the apparatus are as described in the embodiments above.

With reference to one embodiment of the apparatus, when the apparatus is said to "consist essentially of" the named elements, what is meant is that there are no other major components such as a dehydrogenation reactor, or other catalytic reactors; the other optional features described in the specification may be present as well as minor components (fluid lines, pumps, heaters, heated/cooled jacketed fluid lines, etc.) that are well known in the art for effectuating the desired operation.

The invention claimed is:

1. A method of recovering linear butenes from a mixed feed comprising:
    converting an isobutene-to-methyl-t-butylether reactor into a first oligomerization reactor;
    subjecting a first mixed feed to a process to remove polar molecules or molecules containing polar moieties;
    providing the first mixed feed comprising linear butenes and isobutene to the first oligomerization reactor;
    contacting the first mixed feed with an oligomerization catalyst that comprises one or more of MWW family zeolites, and mixtures thereof in the first oligomerization reactor at a temperature in the range of 40 to 105° C. and a space velocity in the range of 2 ml feed/ml catalyst/hour to 12 ml feed/ml catalyst/hour to produce a second mixed feed comprising the linear butenes, $C_8$ olefins and higher oligomers, and a reduced amount of isobutene relative to the first mixed feed; and
    separating the second mixed feed to produce a first effluent of first purified linear butenes, and a second effluent of $C_8$ olefins and higher oligomers; wherein the weight ratio of 2,4,4-trimethyl-1-pentene to 2,4,4-trimethyl-2-pentene in the second effluent decreases within the range from 12.0 to 3.0 when (i) the contacting temperature within the first oligomerization reactor increases within the range from 50° C. to 105° C., (ii) the space velocity decreases within the range from 12 ml feed/ml catalyst/hour to 2 ml feed/ml catalyst/hour, or (iii) both.

2. The method of claim 1, wherein the first mixed feed additionally contains diolefins; and providing a first mixed feed includes hydrogenating the first mixed feed.

3. The method of claim 2, wherein the first mixed feed is at a temperature within the range of from 50 to 150° C. prior to the contacting in the oligomerization reactor.

4. The method of claim 1, wherein the purified linear butenes are further separated to provide a purified 1-butene stream.

5. The method of claim 1, wherein there is no dehydrogenation step after the polars-scrubbing step.

6. The method of claim 1, wherein the first oligomerization reactor temperature is increased from a desirable minimum temperature at a rate within the range of from 1 to 10° C. per 100 hours of contacting up to a desirable upper temperature limit.

7. The method of claim 1, wherein the contacting also includes hydrogen at least every 500 hours of run time for a time of at least 1 hour during continuous run.

8. The method of claim 1, wherein the first effluent of first purified linear butenes comprises less than 0.20 wt % isobutene.

9. The method of claim 1, wherein the first mixed feed comprises from 5 to 60 wt % isobutene.

10. The method of claim 1, wherein a second oligomerization reactor comprising an oligomerization catalyst is fluidly connected to a hydrogenation reactor and a separating unit, in parallel with the first oligomerization reactor but in fluid isolation therefrom until first use.

11. The method of claim 1, wherein there is greater than 30 wt %, by weight of the second mixed feed, of 2,4,4-trimethyl-1-pentene in the second effluent.

* * * * *